(12) United States Patent
Lima (10) Patent No.: US 11,491,004 B2
(45) Date of Patent: Nov. 8, 2022

(54) CARBON NANOTUBE ARTIFICIAL MUSCLE VALVE AND CONNECTIONS

(71) Applicant: Lintec of America, Inc., Richardson, TX (US)

(72) Inventor: Marcio Dias Lima, Richardson, TX (US)

(73) Assignee: LINTEC OF AMERICA, INC., Richardson, TX (US)

( * ) Notice: Subject to any disclaimer, the term of this patent is extended or adjusted under 35 U.S.C. 154(b) by 157 days.

(21) Appl. No.: 16/763,166

(22) PCT Filed: Oct. 26, 2018

(86) PCT No.: PCT/US2018/057740
§ 371 (c)(1),
(2) Date: May 11, 2020

(87) PCT Pub. No.: WO2019/099168
PCT Pub. Date: May 23, 2019

(65) Prior Publication Data
US 2020/0405471 A1 Dec. 31, 2020

Related U.S. Application Data

(60) Provisional application No. 62/646,295, filed on Mar. 21, 2018, provisional application No. 62/597,205, (Continued)

(51) Int. Cl.
*A61F 2/08* (2006.01)

(52) U.S. Cl.
CPC ........ *A61F 2/08* (2013.01); *A61F 2002/0894* (2013.01); *A61F 2220/005* (2013.01); (Continued)

(58) Field of Classification Search
CPC ............. B22F 2302/403; A61F 2/08; A61F 2002/0894; A61F 2220/005; A61F 2250/0036; A61F 2250/0039
See application file for complete search history.

(56) References Cited

U.S. PATENT DOCUMENTS

| 4,620,564 A | 11/1986 | Ekholmer |
| 9,784,249 B2 | 10/2017 | Li et al. |

(Continued)

FOREIGN PATENT DOCUMENTS

| CN | 104769834 | 7/2015 |
| EP | 1787575 | 5/2007 |

(Continued)

OTHER PUBLICATIONS

International Preliminary Report on Patentability issued in corresponding International Application No. PCT/US2018/057740 dated May 19, 2020 (11 pages).

(Continued)

*Primary Examiner* — Jennifer Dieterle
*Assistant Examiner* — Rebecca Lynee Zimmerman
(74) *Attorney, Agent, or Firm* — Greenblum & Bernstein, P.L.C.

(57) ABSTRACT

A carbon nanotube (CNT) artificial muscle valve includes a hollow CNT tube including: a plurality of CNT sheets wrapped in the form of a hollow tube; and a guest material disposed between the CNT sheets and that permeates the CNT sheets. At least one portion of the hollow CNT tube collapses in response to a pressure of a fluid in the hollow CNT tube exceeding a predetermined pressure. The at least one portion of the hollow CNT tube collapses because the at least one portion of the hollow CNT tube generates a torque non-uniformity relative of a remaining portion of the hollow CNT tube.

7 Claims, 9 Drawing Sheets

Related U.S. Application Data filed on Dec. 11, 2017, provisional application No. 62/588,034, filed on Nov. 17, 2017.

(52) U.S. Cl.
CPC ................ *A61F 2250/0036* (2013.01); *A61F 2250/0039* (2013.01)

(56) References Cited

U.S. PATENT DOCUMENTS

| | | |
|---|---|---|
| 9,903,350 B2 | 2/2018 | Li et al. |
| 10,480,491 B2 | 11/2019 | Li et al. |
| 11,143,169 B2 | 10/2021 | Li et al. |
| 11,149,720 B2 | 10/2021 | Li et al. |
| 2012/0032553 A1 | 2/2012 | Goyal et al. |
| 2013/0053958 A1 | 2/2013 | Macossay-Torres |
| 2015/0152852 A1 | 6/2015 | Li et al. |
| 2015/0219078 A1 | 8/2015 | Li et al. |
| 2018/0073490 A1 | 3/2018 | Li et al. |
| 2019/0096540 A1* | 3/2019 | Baughman ............... H01B 1/24 |
| 2020/0088175 A1 | 3/2020 | Li et al. |
| 2020/0191127 A1 | 6/2020 | Li et al. |
| 2022/0003221 A1 | 1/2022 | Li et al. |

FOREIGN PATENT DOCUMENTS

| | | |
|---|---|---|
| EP | 3082248 A2 | 10/2016 |
| JP | 60-159476 | 8/1985 |
| JP | 2012-39741 | 2/2012 |
| JP | 2012-248670 | 12/2012 |
| JP | 2015-533521 | 11/2015 |
| JP | 2017/078461 | 4/2017 |
| WO | 2004/109817 | 12/2004 |
| WO | 2006/028019 | 3/2006 |
| WO | 2011/005375 A2 | 1/2011 |
| WO | 2014/022667 | 2/2014 |
| WO | 2014/022667 A2 | 2/2014 |
| WO | 2017/058339 A2 | 4/2017 |
| WO | 2017/190054 | 11/2017 |

OTHER PUBLICATIONS

International Search Report issued in International Application No. PCT/US2018/057740, dated Apr. 26, 2019 (5 pages).
Written Opinion issued in Application No. PCT/US2018/057740, dated Apr. 26, 2019 (9 pages).
Office Action dated Jul. 5, 2021 issued in Japanese patent application No. 2020-526932 with corresponding English translation.
A. Windle and K. Koziol, Continuous Spinning of Carbon Nanotube Fibres: Structure Control and Properties, Seni Gakkaishi, Japan, 2007, vol. 63, No. 11, pp. P-361 to P-364 (see translation of Office Action).
Office Action dated Jun. 7, 2021 issued in Japanese patent application No. 2020-523347 with corresponding English translation.
Notice of Allowance dated Mar. 7, 2022 issued in Japanese patent application No. 2020-526932, with an English translation.
Notice of allowance dated May 17, 2022 issued in Taiwanese patent application No. 107138071 along with corresponding English translation.

* cited by examiner

CARBON NANOTUBE ARTIFICIAL MUSCLE VALVE AND CONNECTIONS

CROSS REFERENCE TO RELATED APPLICATIONS

This national stage application claims priority to International Patent Application No. PCT/US2018/057740, filed on Oct. 26, 2018, and U.S. Provisional Patent Application Nos. 62/588,034, filed on Nov. 17, 2017, 62/597,205, filed on Dec. 11, 2017, and 62/646,295, filed on Mar. 21, 2018. The contents of these applications are incorporated by reference in their entirety.

BACKGROUND OF INVENTION

Carbone nanotube (CNT) artificial muscle devices (CNT muscles) based on a twisted polymer and CNT fibers/yarns have a wide range of applications. CNT muscles have the advantage of low cost, high production volume, and design simplicity. Additionally, CNT muscles may be advantages over non-CNT muscles for their simple but effective operation.

SUMMARY OF INVENTION

In one aspect, embodiments disclosed herein relate to a carbon nanotube (CNT) artificial muscle valve that includes a hollow CNT tube. The hollow CNT tube includes: a plurality of CNT sheets wrapped in the form of a hollow tube; and a guest material infiltrating between the CNT sheets. At least one portion of the hollow CNT tube falls in at least one of A-C: A. has a thickness less than a thickness of the remaining portion of the hollow CNT tube, B. has an inner diameter that is less than an inner diameter of the remaining portion of the hollow CNT tube, and C. CNTs in the at least one portion are aligned to a bias angle lower than a net bias angle of CNT sheets in the remaining portion of the hollow CNT tube. When a pressure of a fluid in the hollow CNT tube exceeds a predetermined pressure, the at least one portion of the hollow CNT yarn collapses and forms a kink.

In one aspect, embodiments disclosed herein relate to a CNT tube connection that includes: a hollow CNT tube including one or more CNT sheets wrapped in the form of a hollow tube; a rigid tube; and an adhesive applied on an inner surface of an end of the rigid tube. In the CNT tube connection, an end of the hollow CNT tube is disposed inside the end of the rigid tube, the end of the hollow CNT tube is fastened to the rigid tube via the adhesive, and the adhesive infiltrates an outside portion of the end of the hollow CNT tube.

In one aspect, embodiments disclosed herein relate to a method of fastening a hollow CNT tube. The method includes: applying an adhesive onto an inner surface of an end of a rigid tube; disposing an end of the hollow CNT tube inside the end of the rigid tube, wherein the adhesive infiltrates at least a portion of the end of the hollow CNT tube, and wherein the hollow CNT tube comprises one or more CNT sheets wrapped in the form of a hollow tube. The method further includes fastening the end of the hollow CNT tube to the end of the rigid tube via the adhesive.

Other aspects and advantages of one or more embodiments disclosed herein will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to a carbon nanotube (CNT) artificial muscle device that is in form of a hollow tube (hereinafter, hollow CNT tube). Specifically, embodiments of the invention relate to the hollow CNT tube that may be used as a valve to control a flow of a fluid inside the hollow CNT tube, a connection to a hollow CNT tube (e.g., with another tube), and a method for fastening a hollow CNT tube (e.g., to another tube).

Figure 1A:
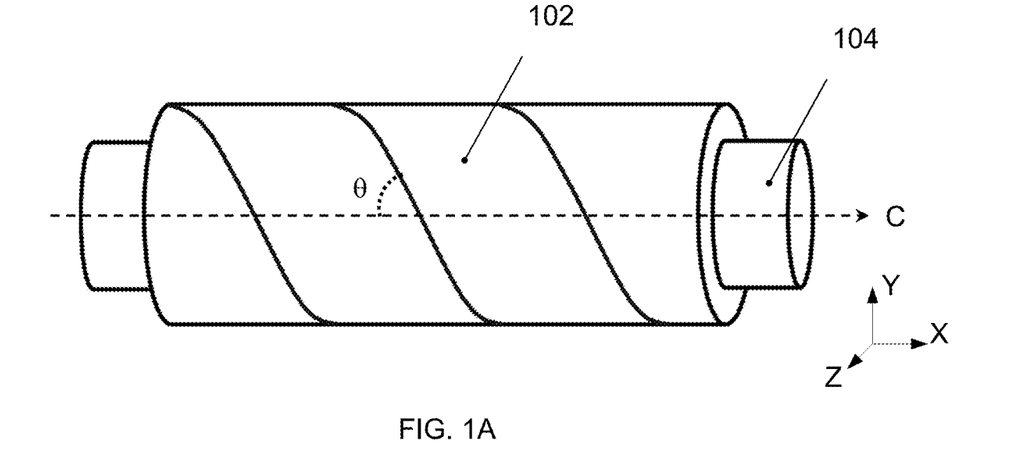
FIG. 1A shows a carbon nanotube (CNT) artificial muscle tube disposed around a mandrel in accordance with one or more embodiments of the invention.

FIG. 1 shows a CNT tube (102) disposed around a core fiber (hereinafter, mandrel (104)). The CNT tube (102) comprises one or more CNT sheets wrapped around the mandrel (104). The CNT sheets are thin sheets of CNTs.

In one or more embodiments, the CNT sheets may be wrapped to create a bias angle "θ" with a central access "C" of the mandrel (104). For example, bias angle of 0° corresponds to the CNT sheets oriented parallel to C, and bias angle of 90° corresponds to the CNT sheets oriented perpendicular to C.

In one or more embodiments, the bias angle is defined by equation (1) below.

$$\theta = \tan^{-1}(2\pi rT) \qquad (1)$$

In equation (1), "r" is the radial distance between CNT sheets and C, and "T" is the number of twists (turns) per meter.

In one or more embodiments, the CNT sheets may be wrapped to have a uniform bias angle across C in a portion or the entire CNT tube (102). Alternatively, in other embodiments, the bias angle may vary across C.

In one or more embodiments, the bias angle may be uniform in a direction perpendicular to C (i.e., radial direction). Alternatively, in other embodiments, the bias angle may vary in the radial direction. For example, the bias angle may increase or decrease monotonically as r increases.

In one or more embodiments, the standard deviation of the bias angle may be less than ±5° in a portion or in the entire CNT tube (102).

In one or more embodiments, the CNT sheets may be wrapped with random bias angles so that the net bias angle is 90° (i.e., there is no bias angle).

In one or more embodiments, the CNT sheets may be wrapped with alternating bias angles (i.e., ±45°) to create the no bias angle condition. For example, one layer of the CNT sheets may be wrapped with bias angle of 45° and another layer of the CNT sheets may be wrapped on the previous layer with bias angle of −45° (or 135°) so the two layers of the CNT sheets cancel their bias angles.

In one or more embodiments, the mandrel (104) may be from, but not limited to, various polymer fibers, metallic wires, carbon fibers, glass fibers, basalt fibers, optical fibers, natural fibers/yarns, another CNT tube, or tows and plies thereof.

In one or more embodiments, the CNT tube (102) includes a guest material infiltrating (permeating) the wrapped CNT sheets. The guest material may infiltrate (permeate) a portion or the entirety of the CNT sheets (e.g., filling cavities in the CNT sheets and between the CNT sheets).

In one or more embodiments, the guest material may be selected based on, but not limited to, its ability to infiltrate the CNT sheets, ability to cover cavities in the CNT tube, melting point, biocompatibility, or durability in hot/cold conditions.

In one or more embodiments, a silicone-based rubber may be used as the guest material because the silicone-based rubber may withstand high temperatures and may not squeeze out of the CNT tube (102) when heated. For example, the guest material may be Sylgard 184 silicone-based rubber or paraffin wax.

In one or more embodiments, the guest material may include, but is not limited to: elastomers such as silicone-based rubber, polyurethane, styrene-butadiene copolymer, and natural rubber; fluorinated plastics such as perfluoroalkoxy alkane (PFA), polytetrafluoroethylene (PTFE), and fluorinated ethylene propylene (FEP); aramids such as Kevlar and nomex; epoxies; polyimides; or paraffin wax.

Figure 1B:
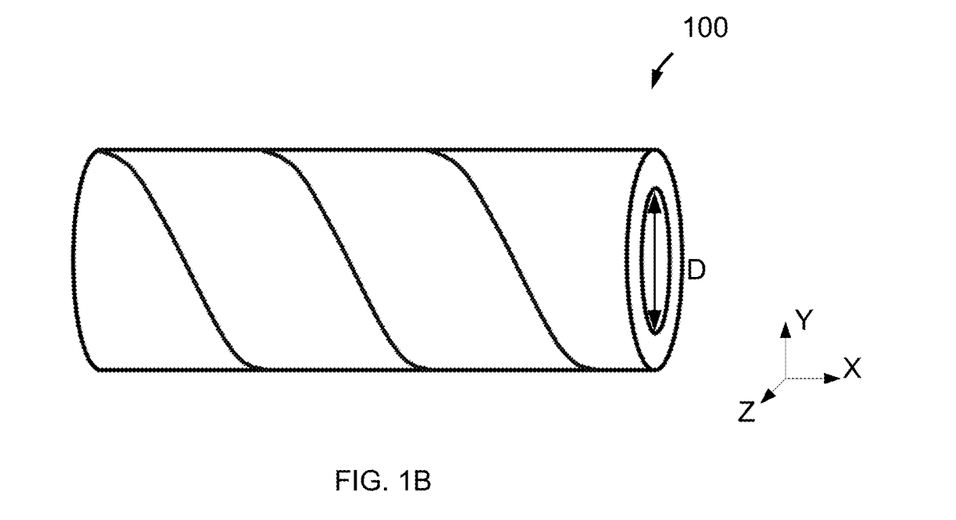
FIG. 1B shows a hollow CNT tube in accordance with one or more embodiments of the invention.

As shown in FIG. 1B, the mandrel (104) shown in FIG. 1A may be removed to create a hollow CNT tube (100). In one or more embodiments, the hollow CNT tube (100) may be the CNT tube (102). In other embodiments, the hollow CNT tube (100) may have additional material such as an interior coating or an exterior coating applied to the interior surface or the exterior surface of the hollow CNT tube (100), respectively.

In one or more embodiments, walls of the hollow CNT tube (100) are sealed such that a fluid inside the hollow CNT tube (100) cannot escape from the walls of the hollow CNT tube (100). For example, the CNT sheets maybe tightly wrapped or the guest material may completely seal the walls of the hollow CNT tube (100).

In one or more embodiments, layers such as graphene sheets/flakes, graphene oxide sheets/flakes, or graphene nanoplatelets may be added between the CNT sheets for example per every 10 CNT sheets or so. These layers may help to seal the hollow CNT tube (100).

In one or more embodiments, when a fluid is inside the hollow CNT tube (100), the fluid may apply an internal radial pressure (hereinafter, internal pressure) on the walls of the hollow CNT tube (100). Because the CNT sheets resist being stretched, the hollow CNT tube (100) resists radial expansion. The hollow CNT tube (100) may resist the internal pressure to a burst pressure of the hollow CNT tube (100).

In one or more embodiments, if the hollow CNT tube (100) has a bias angle, due to the presence of the bias angle and the resistance of the CNT sheets from being stretched, the internal pressure generates a torque on the walls of the hollow CNT tube (100). The generated torque is proportional to the cube of an inner diameter ("D" shown in FIG. 1B) of the hollow CNT tube (100). When the internal pressure reaches a critical value, a portion of hollow CNT tube (100) that is more vulnerable to the torque collapses such that the portion twists along the direction that tightens the twist of the CNT sheets. Thus, the collapse of the vulnerable portion (hereinafter, weak portion) of the hollow CNT tube (100) may limit the flow of the fluid.

Figure 2:
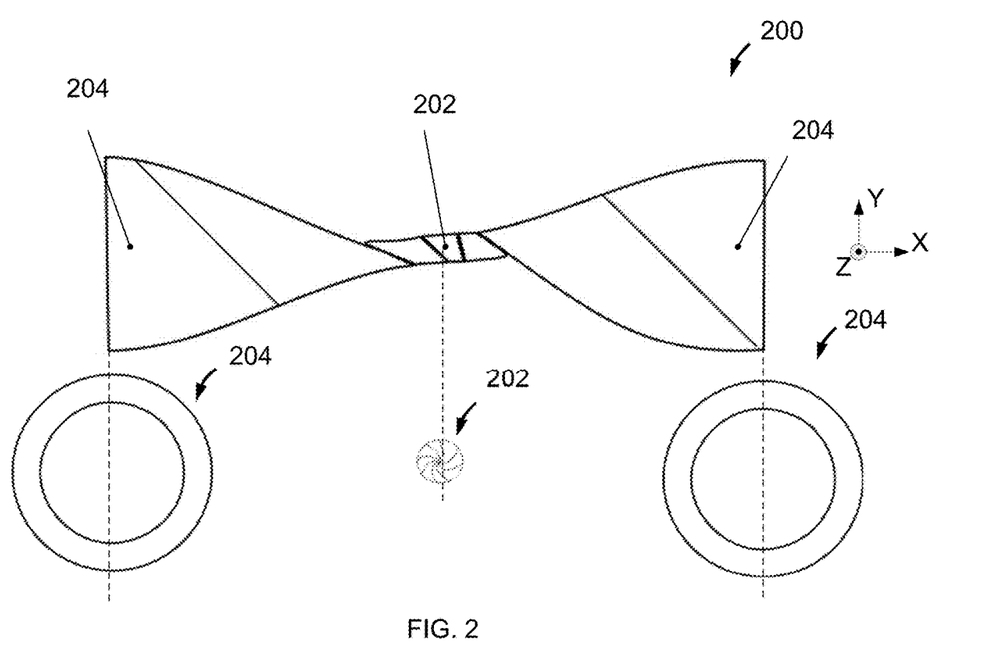
FIG. 2 shows a hollow CNT tube in accordance with one or more embodiments of the invention.

FIG. 2 shows a side view (top) and cross-sectional views (bottom) of the hollow CNT tube (200) in which the weak portion of the hollow CNT tube (200) has collapsed and has formed a kink (202). When the weak portion collapses, the inner diameter of the weak portion decreases (e.g., completely closes or partially closes) and consequently the torque at the weak portion decreases. Accordingly, the non-uniformity of the torque increases, which makes the kink (202) stable. The kink (202) remains stable as long as the fluid applies sufficient internal pressure to the walls of the hollow CNT tube (200). On the other hand, the inner diameter of the remaining portions (204) of the hollow CNT tube (200) may not decrease much compared to the weak portion.

In one or more embodiments, upon the collapse of the weak portion, the fluid flux inside the hollow CNT tube (200) may be completely stopped (e.g., when the inner diameter completely closes). In other embodiments, the fluid flux may be decreased to a value that is predetermined based on the design of the hollow CNT tube (200) (e.g., when the inner diameter partially closes).

In one or more embodiments, the guest material is elastic and when the internal pressure falls down to a predetermined value, the kink (202) opens up.

Figure 3A:
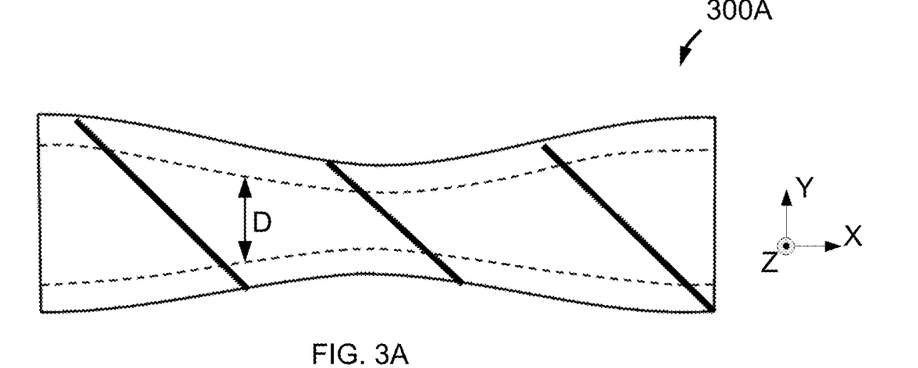
FIGS. 3A-3C show three hollow CNT tubes in accordance with one or more embodiments of the invention.

FIG. 3A shows an example of a weak portion of a hollow CNT tube (300A). In FIG. 3A, the weak portion (the center of the hollow CNT tube (300A)) has an inner diameter smaller than an inner diameter of the remaining portions of the hollow CNT tube (300A). Hereinafter, the weak portion with the smaller diameter is called the "smaller portion."

In one or more embodiments, because the inner diameter (shown as "D" in FIG. 3A) of the hollow CNT tube (300A) in the smaller portion is smaller than the remaining portions, the smaller portion creates less torque than the remaining portions, causing torque non-uniformity. In addition, because of its inner diameter, the smaller portion may be weaker than the remaining portions. The torque non-uniformity across the length of the hollow CNT tube (300A) along with the weakness of the smaller portion causes the smaller portion to collapse and form a kink when the internal pressure exceeds a critical value.

In one or more embodiments, the hollow CNT tube (300A) with the smaller portion may be created by wrapping CNT sheets and creating a CNT tube around a mandrel that has a portion thinner than the remaining of the mandrel. After removing the mandrel from the CNT tube, the hollow CNT tube (300A) with the smaller portion will be created in which the portion of the hollow CNT tube (300A) that was disposed on the thinner portion of the mandrel is the smaller portion. In one or more embodiments, the inner diameter of the smaller portion may be as small as a few micrometers.

Figure 3B:
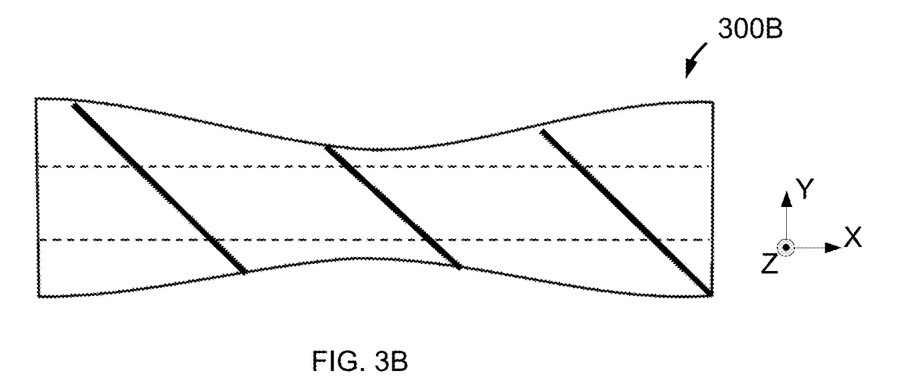

FIG. 3B shows another example of a weak portion of a hollow CNT tube (300B). In FIG. 3B, the weak portion (the center of the hollow CNT tube (300B)) is thinner than the remaining portions of the hollow CNT tube (300B). Hereinafter, the weak portion that is thinner is called the "thinner portion."

In one or more embodiments, the thinner portion may be more vulnerable against twisting. In one or more embodiments, if the inner diameter of the thinner portion is the same as the inner diameter of the remaining portion of the hollow CNT tube (300B), the generated torque may be uniform along the hollow CNT tube (300B). However, because the thinner portion is more vulnerable against twisting, the thinner portion collapses when the inner pressure exceeds a critical value.

In one or more embodiments, the hollow CNT tube (300B) with the thinner portion may be created by wrapping or infiltrating CNT sheets around a mandrel to create a CNT tube that has a portion thinner than the remaining of the CNT tube. After removing the mandrel from the CNT tube, the hollow CNT tube (300B) with the thinner portion will be created.

Figure 3C:
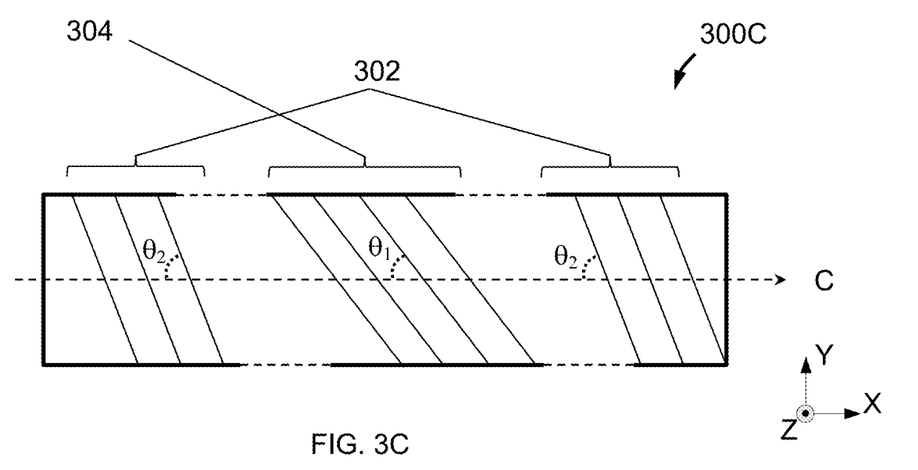

FIG. 3C shows another example of a weak portion of a hollow CNT tube (300C). In FIG. 3C, the weak portion has a bias angle "$\theta_1$" different from the bias angle "$\theta_2$" of the remaining portions (302) of the hollow CNT tube (300C). Hereinafter, the weak portion that has a different bias angle is called the "biased portion (304)".

In one or more embodiments, at bias angles close to 0° and 90°, the theoretical generated torque approaches 0 and at a bias angle close to 54.73° the theoretical generated torque is maximized. Therefore, the bias angle of the biased portion (304) may be designed appropriately to generate a different torque than the remaining portions (302) and cause torque non-uniformity across the hollow CNT tube (300C). The torque non-uniformity may force the hollow CNT tube (300C) to collapse at a weak portion when the internal pressure exceeds a critical value.

In one or more embodiments, the strength of the hollow CNT tube (300C) against torsion depends on the bias angle. In one or more embodiments, a portion of the hollow CNT tube (300C) that has a smaller bias angle (closer to) 0° may be weaker against torsion than a portion with larger bias angle (closer to 90°). Therefore, the weak portion may be the portion that has a smaller bias angle than the remaining portion of the hollow CNT tube (300C). Accordingly, as shown in FIG. 3C, the biased portion (304) may have a lower bias angle than the remaining portions (302) so that the biased portion (304) is a weak portion.

In one or more embodiments, a weak portion may be, but not limited to, any combinations of the smaller portion, the thinner portion, and the biased portion (304) disclosed above.

In one or more embodiments, the hollow CNT tubes (300A, 300B, 300C) may have a plurality of weak portions across the length of the hollow CNT tube (300A, 300B, 300C).

Figure 4:
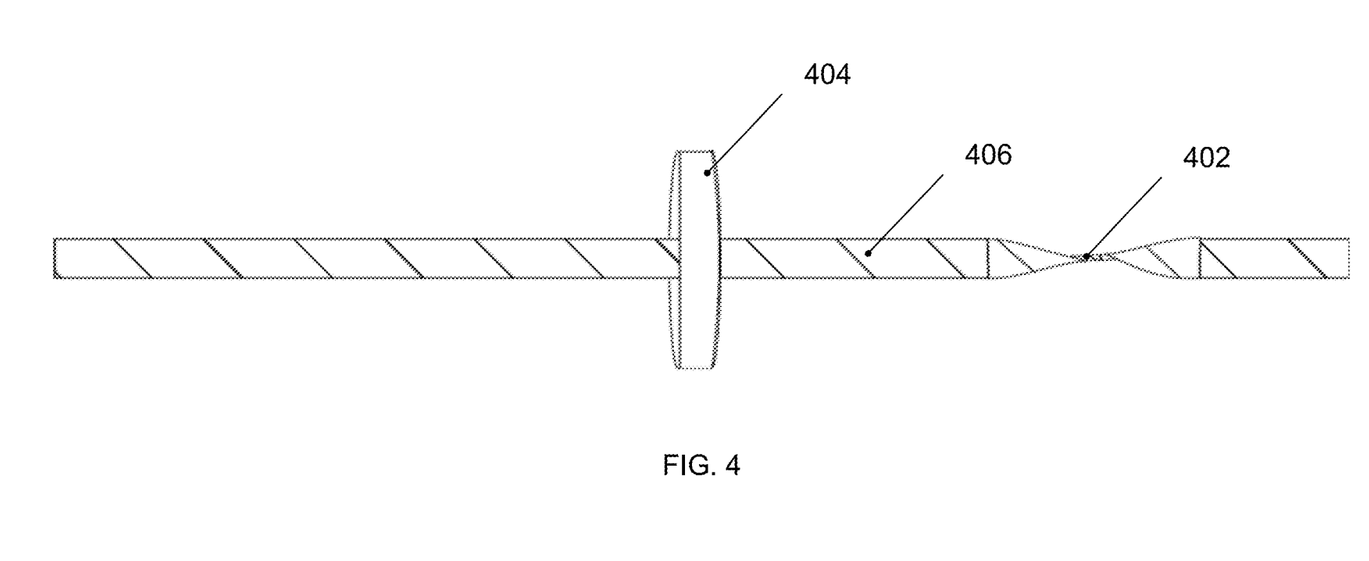
FIG. 4 shows a system for collapsing a portion of a hollow CNT tube in accordance with one or more embodiments of the invention.

FIG. 4 shows that a kink (402) may be initiated by a motor (404) that twists a hollow CNT tube (406). In one or more embodiments, to initiate the kink (402), the motor (404) twists the hollow CNT tube (406) in a direction along the twist of the CNT sheets (i.e., the direction that tightens the CNT sheets). When the kink (402) is initiated, because the initiated kink now has a smaller inner diameter than the remaining portion, the torque non-uniformity is induced in the hollow CNT tube (406). The torque non-uniformity fully collapses the hollow CNT tube (406) and creates a stable kink (402). In these embodiments, the hollow CNT tube (406) may have a uniform thickness, inner diameter, or bias angle.

In one or more embodiments, because the induced torque non-uniformity helps the motor (404) to create the kink (402), even a weak motor (404) may be sufficient.

In one or more embodiments, a plurality of motors (404) may be disposed on the hollow CNT tube (406).

In one or more embodiments, the kink (402) may be opened by untwisting the hollow CNT tube (406) via the motor (404). For example, the motor (404) may rotate the hollow CNT tube (406) in a direction opposite to the twisting direction of the hollow CNT tube (406).

In one or more embodiments, flexibility of the hollow CNT tube makes it uniquely suitable for the kink formation via the motor (404).

In one or more embodiments, to incorporate hollow CNT tubes in fluidic networks hollow CNT tubes may be fastened in various connections.

Typically, polymeric tubes such as hoses cannot be soldered or glued, making connections to the polymeric tubes unreliable. Also, adhesives do not easily infiltrate the polymeric tubes and thus, do not adhere to the polymeric tubes properly. Few adhesives can effectively adhere to tubes made of vulcanized rubbers, none of which are satisfactory.

In one or more embodiments, a hollow CNT tube may have networks of CNTs with many open spaces that let the adhesive infiltrate into walls of the hollow CNT tubes.

Figure 5:
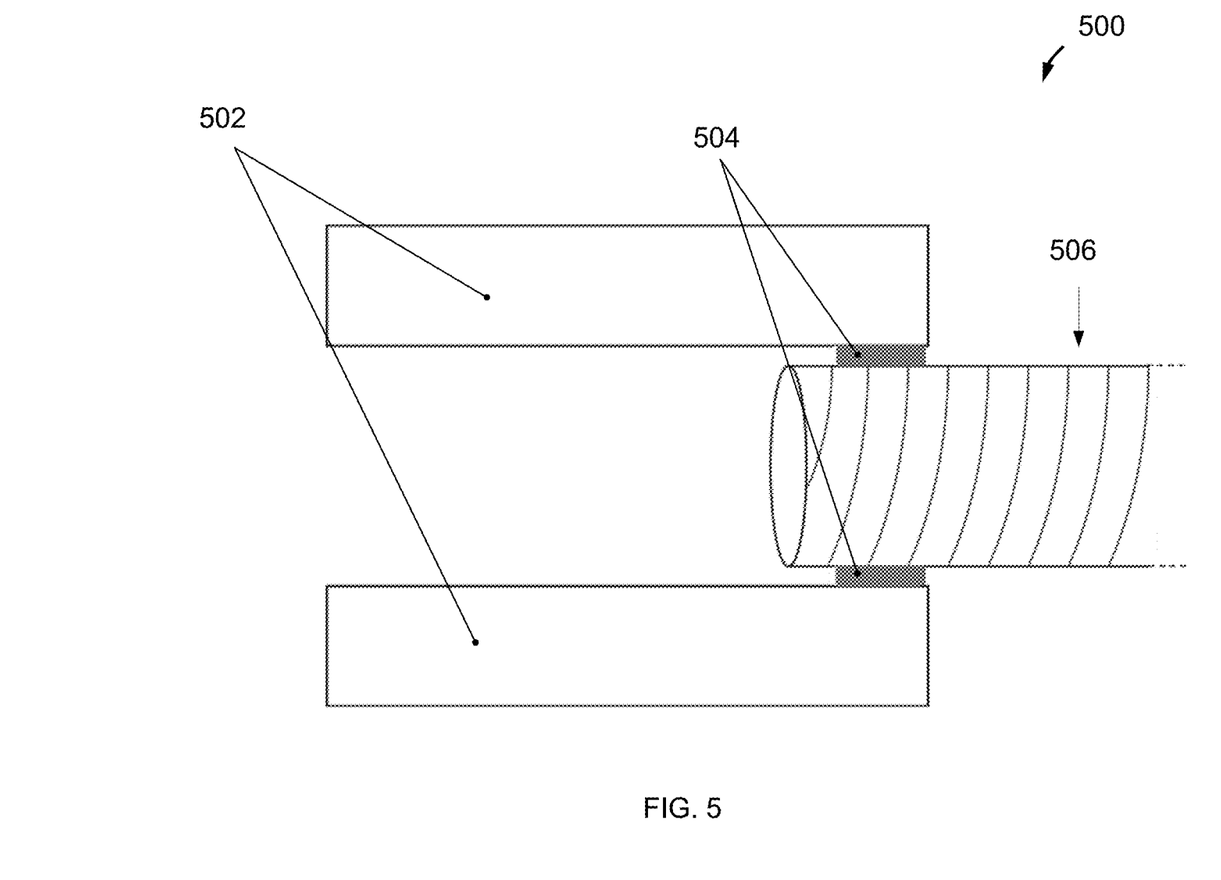
FIG. 5 shows a connection between a rigid tube and a hollow CNT tube in accordance with one or more embodiments of the invention.

FIG. 5 shows a connection (500) between a rigid tube (502) and a hollow CNT tube (506). In one or more embodiments, the rigid tube (502) may be a metallic tube or a rigid polymeric tube. In one or more embodiments, the rigid tube (502) may be a tube that is less flexible than the hollow CNT tube (506).

An adhesive (504) is disposed on an inner surface of an end of the rigid tube (502) (hereinafter, the "sticky end"). One end of the hollow CNT tube (506) (hereinafter, the "fastening end") fits inside the sticky end of the rigid tube (502). In one or more embodiments, when the adhesive (504) dries, the adhesive (504) becomes solid and firmly holds the fastening end of the hollow CNT tube (506) inside the sticky end of the rigid tube (502).

In one or more embodiments, the adhesive (504) may seal the connection (500) such that a liquid inside the rigid and the hollow CNT tubes (502, 506) cannot leak through that connection (500).

In one or more embodiments, the adhesive (504) may be a type of hot-melt glue and may be heated to stick to the fastening end of the hollow CNT tube (506). Then, the hot-melt glue adhesive (506) cools, becomes solid, and firmly fastens the hollow CNT tube (506) to the rigid tube (502).

In one or more embodiments, CNT sheets in the outer layers of the fastening end of the hollow CNT tube (506), in at least a portion that contacts the adhesive (504), will not have been infiltrated by the guest material or densified. The non-infiltrated/non-densified portion allows the adhesive (504) to infiltrate the CNT sheets in these portions and provide a strong adhesion.

In one or more embodiments, the adhesive (504) may penetrate into the CNT sheets to at least 5% and up to 99% of the thickness of the hollow CNT tube (506).

In one or more embodiments, an inner portion of at least the fastening end of the hollow CNT tube (506) may be treated with a fluoropolymer. The fluoropolymer may block the adhesive (504) from infiltrating into the inner portion of the fastening end of the hollow CNT tube (506).

In one or more embodiments, the fluoropolymer may include, but not limited to, any combination of materials from a group consisting of: polytetrafluoroethylene (PTFE), perfluoroalkoxy alkane (PFA), fluorinated ethylene propylene (FEP), ethylene tetra fluoroethylene (ETFE), polyvinylidene fluoride (PVDF), and ethylene chlorotrifluoroethylene (ECTFE).

Figure 6:
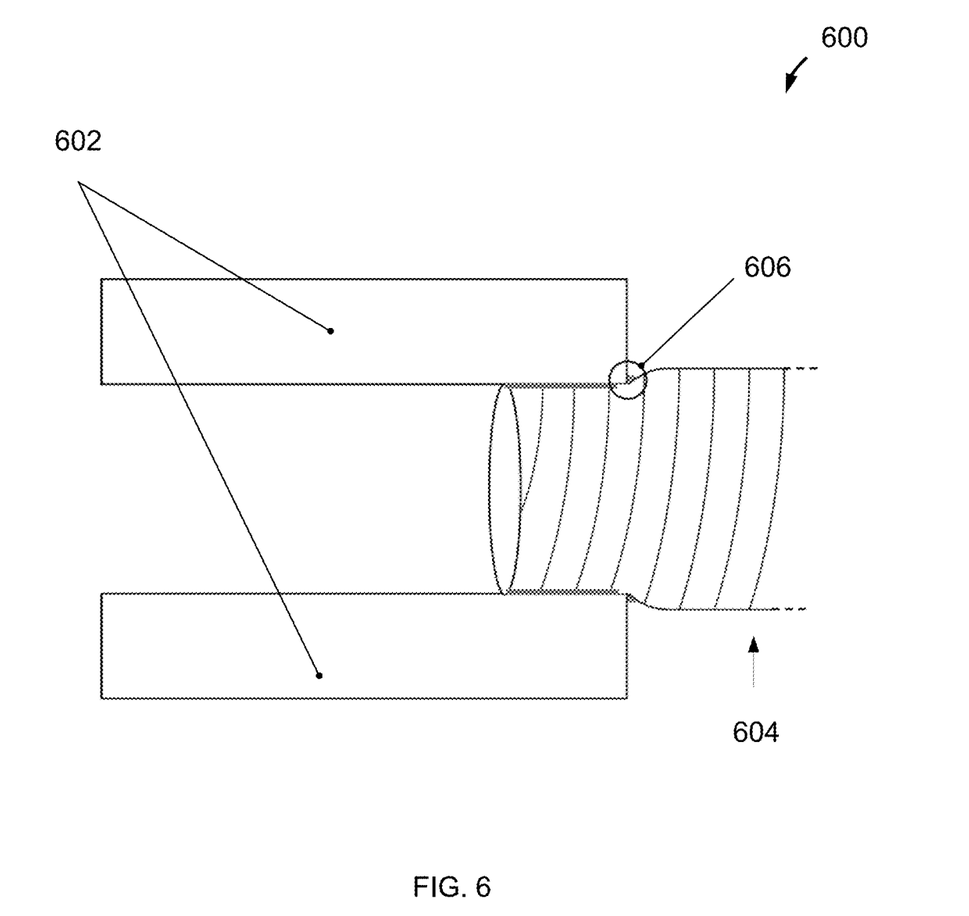
FIG. 6 shows a connection between a rigid tube and a hollow CNT tube in accordance with one or more embodiments of the invention.

FIG. 6 shows a connection (600) in which the sticky end of the rigid tube (602) has a sharp edge in the vicinity of or in contact with the hollow CNT tube (604). When a fluid inside the hollow CNT tube (604) applies an internal pressure, the hollow CNT tube (604) may expand. The sticky end of the rigid tube (602) prevents expansion of the fastening end of the hollow CNT tube (604). However, the portion of the hollow CNT tube (604) that is not in the rigid tube (602) may expand. Thus, the sharp edge of the rigid tube (602) applies a stress on the hollow CNT tube (604). Hereinafter, the portion of the hollow CNT tube (604) that is stressed by the sharp edge is called "stress point" (606). The stress point (606) may decrease the lifetime of the hollow CNT tube (604) by being torn after several expansion cycles.

Figure 7:
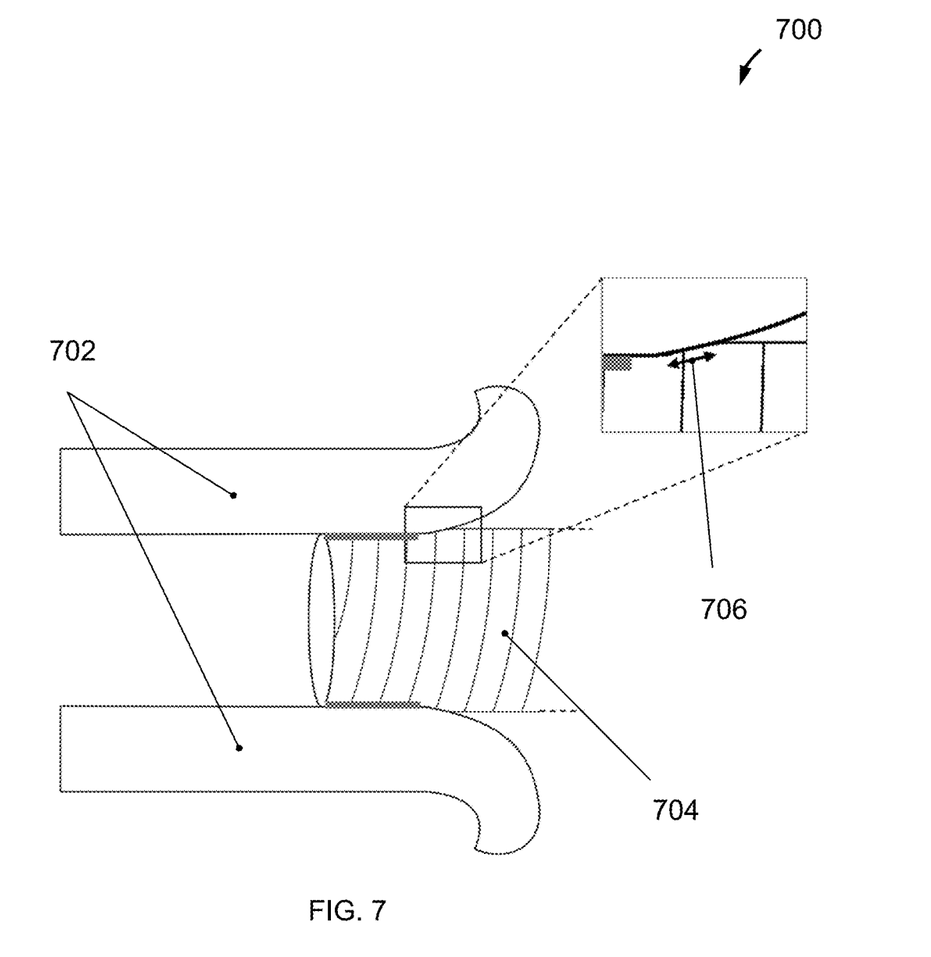
FIG. 7 shows a connection between a rigid tube and a hollow CNT tube in accordance with one or more embodiments of the invention.

FIG. 7 shows a connection (700) in which the sticky end of the rigid tube (702) has a curved surface in vicinity of or in contact with the hollow CNT tube (704). Upon application of an internal pressure from the fluid, when the hollow CNT tube (704) expands, the curved surface of the rigid tube (702) allows for a smooth transition in the outer diameter of the hollow CNT tube (704) and reduces stress on the hollow CNT tube (704). The close-up portion of FIG. 7 shows the smoothly expanded part (706) of the hollow CNT tube (704).

In one or more embodiments, the curved surface of the rigid tube (702) may have a curvature that is 0.5 to 3 times of an outer radius of the fastening end of the hollow CNT tube (704).

In one or more embodiments, the sticky end of the rigid tube (702) has a funnel shape, as shown in FIG. 7.

Figure 8A:
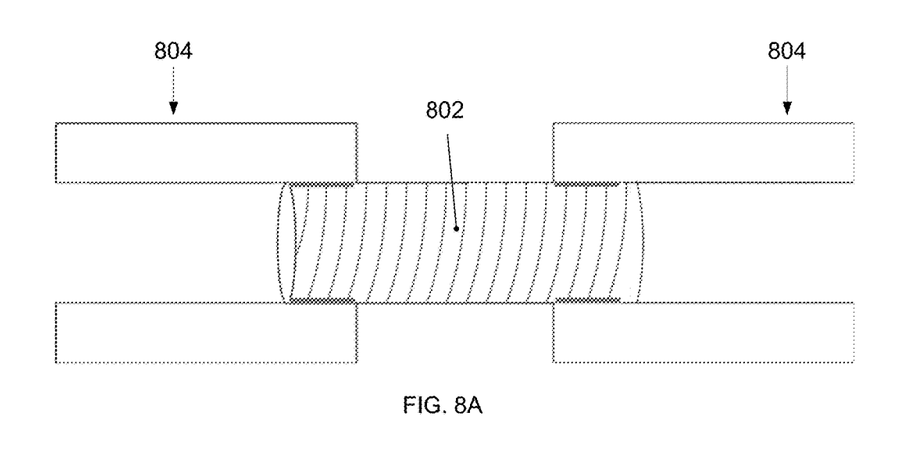
FIGS. 8A and 8B show connections between rigid tubes and hollow CNT tubes in accordance with one or more embodiments of the invention.
Figure 8B:
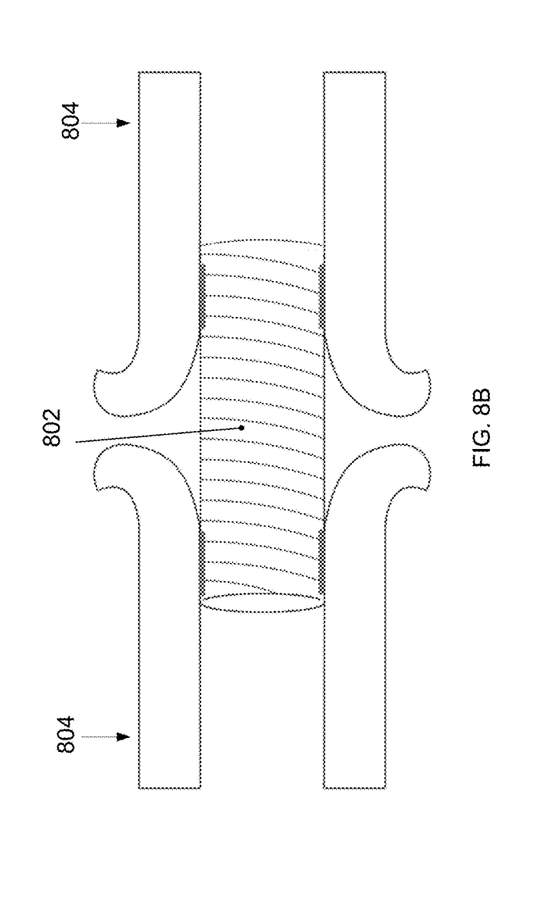

FIGS. 8A and 8B show implementation examples in accordance with one or more embodiments. In each of FIGS. 8A and 8B, the hollow CNT tube (802) is fastened to two rigid tubes (804). In FIGS. 8A and 8B, only parts of the rigid tubes (804) are shown for simplification of illustration. However, both ends of each of the rigid tubes (804) may be modified as disclose in the above embodiments to connect an end of a hollow CNT tube to an end of another hollow CNT tube. Accordingly, multiple connections may be created to fasten multiple hollow CNT tubes with multiple rigid tubes.

A connector in accordance with one or more embodiments may have a plurality of connections disclosed in the above embodiments such that the connector may connect a plurality of hollow CNT tubes together. For example, the connector may have a plurality of rigid tubes connected to each other in a specific way to form a three-dimensional connection.

The connections/connectors disclosed in accordance with one or more embodiments herein may be used for fastening/connecting micro-tubes such as micro-tube actuators in micro-fluid applications, hydraulic systems, micro-cooling systems, drug delivery systems, or pneumatic systems.

Figure 9:
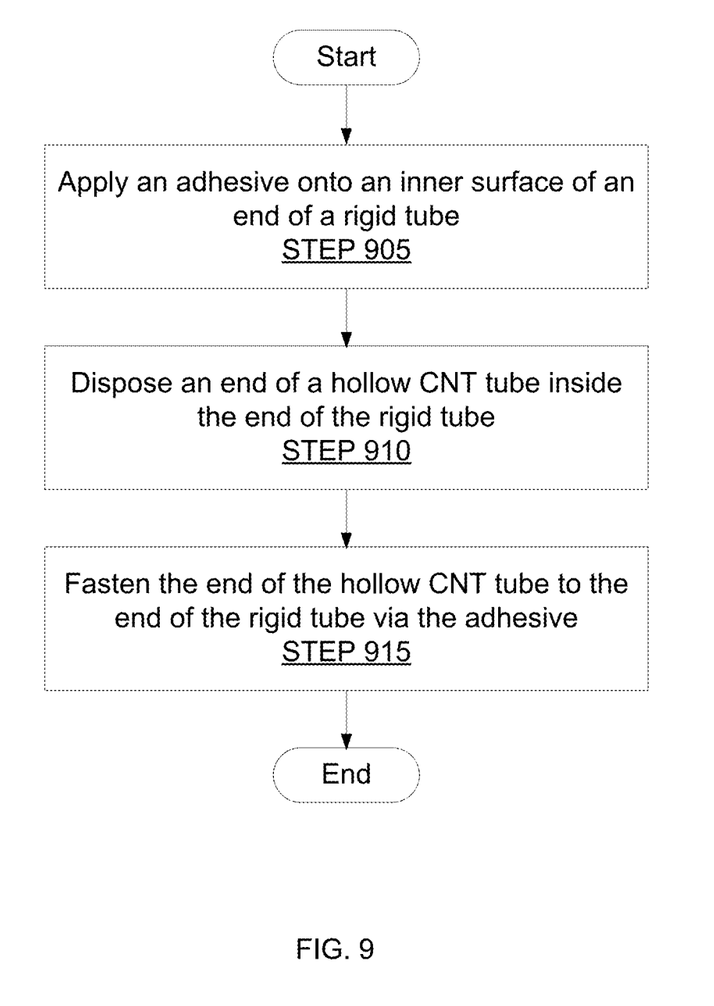
FIG. 9 shows a flowchart in accordance with one or more embodiments of the invention.

FIG. 9 shows a flow chart depicting a method for fastening a hollow CNT tube. In one or more embodiments, one or more of the steps shown in FIG. 9 may be omitted, repeated, and/or performed in a different order than the order shown in FIG. 9. Accordingly, the scope of the invention is not limited to the specific arrangement of steps shown in FIG. 9.

In STEP 905, an adhesive is applied to an inner surface of an end of a rigid tube. For example, as shown in FIG. 5, the adhesive (504) is applied to the sticky end of the rigid tube (502).

In STEP 910, an end of a hollow CNT tube is disposed inside the end of the rigid tube that is covered with the adhesive. For example, as shown in FIG. 5, the fastening end of the hollow CNT tube (506) is disposed in the sticky end of the rigid tube (502).

In STEP 915, the end of the hollow CNT tube is fastened to the end of the rigid tube. For example, as disclosed above, an adhesive may infiltrate the CNT sheets of a fastening end of a hollow CNT tube. In another example, the adhesive may be heated to melt and infiltrate CNT sheets of the hollow CNT tube.

In addition, as disclosed above, an inner portion of the end of the hollow CNT tube may be treated with a fluoropolymer to block the adhesive from infiltrating the inner portion of the hollow CNT tube.

Further, as disclosed above with reference to FIG. 7, the end of the rigid tube may be curved to reduce a stress on the hollow CNT tube.

In one or more embodiments, the hollow CNT tubes and the connections/connectors described above may be connected together to realize micro-tube actuating systems or fluidic networks such as micro-fluidic networks, drug delivery systems, hydraulic systems, or pneumatic systems.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A carbon nanotube (CNT) artificial muscle valve comprising:
  a hollow CNT tube comprising:
    a plurality of CNT sheets wrapped in a form of a hollow tube having a hollow tube CNT sheet wrapping direction, a hollow tube inner diameter, a hollow tube wall thickness, a hollow tube central axis direction being a direction from a first end of the hollow tube to an opposite second end of the hollow tube, and a hollow tube bias angle between the hollow tube CNT sheet wrapping direction and the hollow tube central axis direction, the hollow tube further having at least one inner portion having an inner portion inner diameter, an inner portion wall thickness, and an inner portion bias angle of an inner portion CNT sheet wrapping direction relative to the hollow tube central axis direction; and a guest material disposed between the CNT sheets and that permeates the CNT sheets, wherein the hollow tube bias angle is greater than 0° and less than 90°, the inner portion bias angle is greater than 0° and less than 90°, and the at least one inner portion has at least one of A-C:
A. the inner portion wall thickness is less than the hollow tube wall thickness,
B. the inner portion inner diameter is less than the hollow tube inner diameter, and
C. the inner portion bias angle is less than the hollow tube bias angle, and the at least one inner portion collapses in response to a pressure of a fluid inside the hollow CNT tube flowing along the hollow tube central axis direction, the pressure exceeding a predetermined pressure.

2. The CNT artificial muscle valve according to claim 1, wherein the collapse of the at least one inner portion completely closes by reducing the inner portion inner diameter to zero and stops the flow of the fluid completely.

3. The CNT artificial muscle valve according to claim 1, wherein the collapse of the at least one inner portion reduces the inner portion inner diameter to a value greater than zero and decreases the flow of the fluid.

4. The CNT artificial muscle valve of claim 1, further comprising at least one motor disposed on the hollow tube, wherein the at least one motor twists the hollow tube in the hollow tube CNT sheet wrapping direction thereby decreasing the inner portion inner diameter.

5. The CNT artificial muscle valve of claim 1, wherein the motor untwists the hollow tube in a direction opposite to the hollow tube CNT sheet wrapping direction and increase the inner portion inner diameter.

6. The CNT artificial muscle valve of claim 1, further comprising a first straight hollow rigid tube connecting to the first end of the hollow tube.

7. The CNT artificial muscle valve of claim 1, further comprising a first straight hollow rigid tube connecting to the second end of the hollow tube.

\* \* \* \* \*